United States Patent
Rioux

(10) Patent No.: US 8,652,022 B2
(45) Date of Patent: Feb. 18, 2014

(54) STABILIZER AND METHOD FOR IRRADIATING TUMORS

(75) Inventor: Robert Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1006 days.

(21) Appl. No.: 12/208,224

(22) Filed: Sep. 10, 2008

(65) Prior Publication Data

US 2009/0069624 A1   Mar. 12, 2009

Related U.S. Application Data

(60) Provisional application No. 60/971,218, filed on Sep. 10, 2007.

(51) Int. Cl.
*A61N 5/02* (2006.01)
(52) U.S. Cl.
USPC .............................................. 600/2
(58) Field of Classification Search
USPC .................. 600/1–8, 427; 604/500
See application file for complete search history.

(56) References Cited

U.S. PATENT DOCUMENTS

| | | | |
|---|---|---|---|
| 373,362 | A | 11/1887 | Hamilton |
| 4,143,652 | A | 3/1979 | Meier et al. |
| 4,580,561 | A | 4/1986 | Williamson |
| 4,863,133 | A | 9/1989 | Bonnell |
| 5,534,778 | A | 7/1996 | Loos et al. |
| 5,571,084 | A | 11/1996 | Palmer |
| 5,597,146 | A | 1/1997 | Putnam |
| 5,702,405 | A | 12/1997 | Heywang-Koebrunner |
| 5,706,812 | A | 1/1998 | Strenk et al. |
| 5,833,627 | A | 11/1998 | Shmulewitz et al. |
| 5,868,740 | A | 2/1999 | LeVeen et al. |
| 5,913,863 | A | 6/1999 | Fischer et al. |
| 6,050,954 | A | 4/2000 | Mittermeier |
| 6,085,749 | A | 7/2000 | Wardle et al. |
| 6,146,377 | A | 11/2000 | Lee et al. |
| 6,203,499 | B1 | 3/2001 | Imling et al. |
| 6,287,521 | B1 | 9/2001 | Quay et al. |
| 6,304,770 | B1 | 10/2001 | Lee et al. |
| 6,440,100 | B1 | 8/2002 | Prentiss |
| 6,491,273 | B2 | 12/2002 | King et al. |

(Continued)

FOREIGN PATENT DOCUMENTS

| | | |
|---|---|---|
| EP | 0 995 399 A1 | 4/2000 |
| WO | WO 02/38032 A2 | 5/2002 |

OTHER PUBLICATIONS

Bucsko, J.K., Managing Respiratory Motion, Radiology Today 5(23):33 (2004).

Primary Examiner — Christine Matthews
(74) Attorney, Agent, or Firm — Bingham McCutchen LLP

(57) ABSTRACT

A method of treating a region of diseased tissue using a probe is disclosed. A probe cannula is introduced into the tissue of the patient until a distal end of the cannula is located at or proximate to the treatment region. A plurality of electrodes are then deployed from the distal end of the cannula into the treatment region. Energy (e.g., radiofrequency energy) is then delivered through the plurality of electrodes to the tissue. The cannula is then secured to an immobile object external to the patient. The treatment region is irradiated with a therapeutically effective dose of an ionizing radiation while the plurality of electrodes remain at least partially advanced within the treatment region and while the cannula remains secured to the immobile object.

23 Claims, 5 Drawing Sheets

(56) References Cited

U.S. PATENT DOCUMENTS

| | | |
|---|---|---|
| 6,569,176 B2 | 5/2003 | Jesseph |
| 6,577,702 B1 | 6/2003 | Lebovic et al. |
| 6,589,254 B2 | 7/2003 | Fontenot |
| 6,632,170 B1 | 10/2003 | Bohanan et al. |
| 6,676,610 B2 | 1/2004 | Morton et al. |
| 6,834,837 B2 | 12/2004 | Schilt et al. |
| 2002/0026126 A1 | 2/2002 | Burdorff et al. |
| 2003/0130575 A1 | 7/2003 | Desai |
| 2003/0153802 A1* | 8/2003 | Bonan et al. ............ 600/3 |
| 2003/0229282 A1* | 12/2003 | Burdette et al. ........ 600/439 |
| 2004/0215101 A1 | 10/2004 | Rioux et al. |
| 2004/0254572 A1 | 12/2004 | McIntyre et al. |
| 2006/0058598 A1 | 3/2006 | Esposito |
| 2006/0217587 A1* | 9/2006 | DiCarlo et al. ............ 600/1 |

\* cited by examiner

STABILIZER AND METHOD FOR IRRADIATING TUMORS

RELATED APPLICATION DATA

The present application claims the benefit under 35 U.S.C. §119 to U.S. provisional patent application Ser. No. 60/971,218, filed Sep. 10, 2007. The foregoing application is hereby incorporated by reference into the present application in its entirety

FIELD OF THE INVENTION

The present invention is in the field of medical devices, and particularly in the field of stabilizers to immobilize tumors prior to irradiation.

BACKGROUND

During radiation therapy, the radiation is delivered in a targeted beam to the tumor. However, due to normal physiological function, the patient's body is in constant motion. Breathing and heart function cause the body, and in particular the chest and the abdomen, of the patient to move. The constant motion can distort target volumes and result in positioning errors, particularly in abdominal, lung, liver, and breast cancer tumors. It is estimated that abdominal tumors move approximately 2 millimeters, while lunch tumors move on average from 3 to 22 millimeters during breathing. Bucsko, J. K. "Managing Respiratory Motion", *Radiology Today* 5(23): 33 (2004). It is therefore desirable to immobilize tumors prior to and during the radiation therapy.

SUMMARY OF THE INVENTION

The present disclosure relates to methods of treating a treatment region within solid tissue of a patient using a probe, the probe having a cannula and a handle, the cannula having a distal end, where the method includes introducing the cannula into the solid tissue of the patient until the distal end of the cannula is located proximate to the treatment region; advancing a plurality of electrodes from the distal end of the cannula into the treatment region; delivering energy through the plurality of electrodes; securing the cannula to an immobile object external to the patient; and irradiating the treatment region with a therapeutically effective dose of an ionizing radiation while the plurality of electrodes remain at least partially advanced within the treatment region and while the cannula remains secured to the immobile object.

The plurality of electrodes can preferably be advanced in a generally distal direction from the distal end of the cannula within the treatment region. In preferred embodiments, the electrodes diverge, curve radially outwardly, and evert to form a three-dimensional pattern from the distal end of the cannula. Typically, the plurality of electrodes can be advanced symmetrically about an axis extending from the distal end of the cannula into the treatment region.

The treatment region can be a malignant tumor. The solid tissue can be selected from the group consisting of lung, liver, breast, and tissue within the abdominal cavity.

Typically, energy can be delivered by establishing radio frequency current flow among the plurality of electrodes.

Preferably, after the cannula is secured to an immobile object and the plurality of electrodes are extended into the treatment region, the plurality of electrodes hold the treatment region substantially stationary relative to the distal end of the cannula.

In some embodiments, the handle is secured to the immobile object, while alternatively, the cannula is secured to the immobile object. While the probe is secured to the immobile object the distal end of the cannula is held substantially stationary relative to the immobile object. The immobile object can be a bed, a bed frame, or a lattice frame positioned over the bed. The cannula can be secured to the immobile object at any point prior to the irradiation step. Thus, the cannula can be secured prior to delivering energy, or alternatively, after delivering energy.

Typically the ionizing radiation is selected from the group consisting of x-ray, gamma ray, electron beam, protons, neutrons, alpha particles, and beta particles.

Preferably, the plurality of electrodes are retracted into the cannula and the cannula is removed from the patient after the treatment region is irradiated.

Alternatively, the present disclosure relates to a method of treating a treatment region within solid tissue of a patient using a probe, the probe having a cannula and a handle, the cannula having a distal end, where the method includes introducing the cannula into the solid tissue of the patient until the distal end of the cannula is located proximate to the treatment region; advancing a plurality of electrodes from the distal end of the cannula into the treatment region; delivering energy through the plurality of electrodes; securing the cannula to an immobile object external to the patient, whereby the distal end of the cannula remains substantially stationary relative to the immobile object; and irradiating the treatment region with a therapeutically effective dose of an ionizing radiation while the plurality of electrodes remain at least partially advanced within the treatment region and while the cannula remains secured to the immobile object.

In another embodiment, the present disclosure relates to a method of treating a treatment region within solid tissue of a patient using a probe, the probe having a cannula and a handle, the cannula having a distal end, where the method includes introducing the cannula into the solid tissue of the patient until the distal end of the cannula is located proximate to the treatment region; advancing a plurality of electrodes through the cannula into the solid tissue in a generally distal direction from the distal end of the cannula within the treatment region, wherein the electrodes diverge, curve radially outwardly, and evert to form a three-dimensional pattern from the distal end of the cannula, whereby the plurality of electrodes hold the treatment region substantially stationary relative to the distal end of the cannula; establishing radio frequency current flow among the plurality of electrodes; securing the cannula to an immobile object external to the patient, whereby the distal end of the cannula remains substantially stationary relative to the immobile object; irradiating the treatment region with a therapeutically effective dose of an ionizing radiation while the plurality of electrodes remain at least partially advanced within the treatment region and while the cannula remains secured to the immobile object; and retracting the plurality of electrodes into the cannula and removing the cannula from the patient after irradiating the treatment region.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Methods of treating certain types of cancer, such as lung cancer, liver cancer, or abdominal cancer, include heating the cancerous tumor with radiofrequency (RF) and then irradiating the tumor with radiation. It has been found that the combination of RF treatment followed by radiation treatment is effective in destroying tumors and reducing their size. Methods disclosed herein are directed to inserting an RF probe into a tumor, locking it in place, and performing ablation. The RF probe, when left in place, can act to immobilize the tumor for the irradiation step.

While some embodiments of RF probes are described herein, the present invention works well with multi-tined RF probes known in the art, such as those described in U.S. Pat. No. 5,868,740, which is incorporated by reference herein in its entirety. One family of commercially available RF ablation probes that can be used with the methods described herein are the LeVeen® Needle Electrode and the LeVeen CoAccess™-Electrode System (collectively referred to herein as the "LeVeen ablation probe"), manufactured and distributed by Boston Scientific Corporation (www.bostonscientific.com). The LeVeen ablation probe comprises an array of elongate wire electrode elements that are deployable from a distal portion of an elongate delivery cannula. A handle is connected to a proximal portion of the delivery cannula, and a plunger is coupled in a reciprocating fashion to the handle. In particular, the plunger is fixedly coupled to the electrode array elements such that, when the plunger is extended proximally relative to the handle, the electrode elements are withdrawn into the cannula, and when the plunger is depressed distally into the handle, the electrode elements are deployed out of the cannula.

Figure 1:
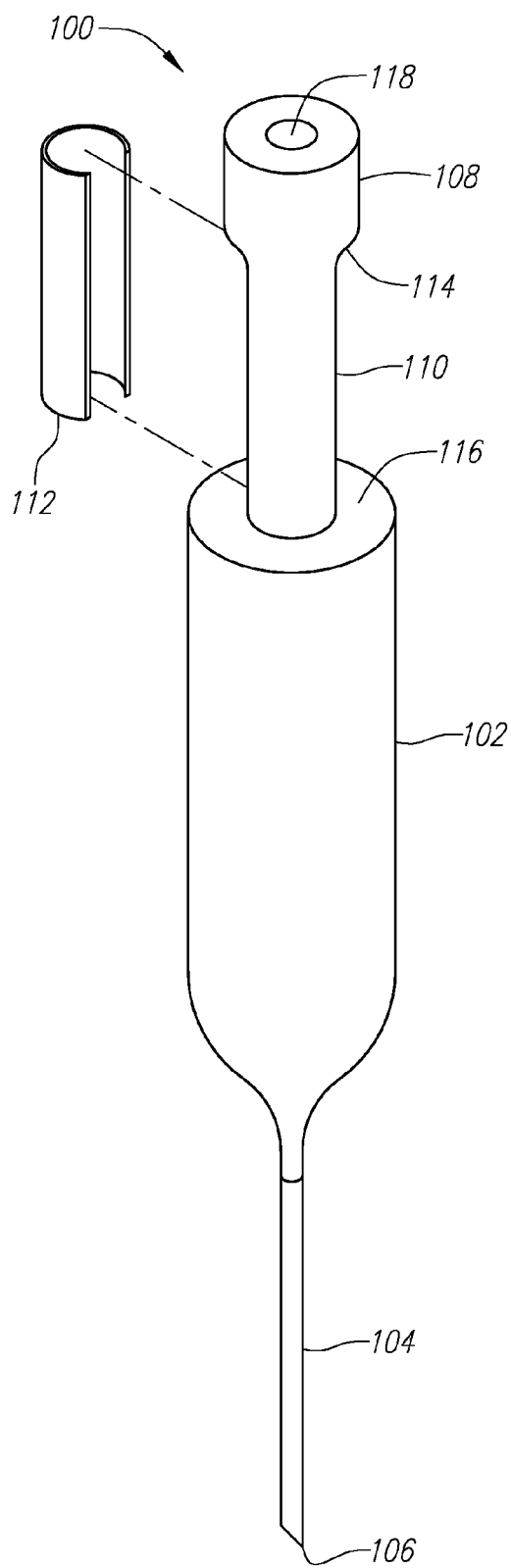
FIG. 1 shows an embodiment of an RF probe.

Referring now to FIG. 1, an embodiment of an RF probe 100 is shown, having a handle 102 and a cannula 104. Handle 102 is preferably constructed from plastic, but it can also be constructed from metal. Handle 102 is a generally hollow cylinder. As seen in FIG. 1, the diameter of handle 102 tapers at its distal end until it closely approximates the diameter of cannula 104.

A cylindrical plunger 110 is concentrically nestled within handle 102. Plunger 110 can move longitudinally within handle 102. At the proximal end of plunger 110, a handle 108 has a larger diameter than plunger 110.

The distal end 106 of cannula 104 terminates in a sharp point that can penetrate skin and tissue. Preferably, distal end 106 of cannula 104 is a beveled tip. Cannula 104 is constructed from material that can come into contact with the internal tissues in a human body without causing substantial adverse allergic reaction. Examples of such material include a variety of plastics and metals, such as aluminum, titanium, and stainless steel. Preferably, cannula 104 is constructed from metal. Cannula 104 is of sufficient rigidity that it does not bend when pressure is applied to insert it into human tissue. Preferably, cannula 104 is sheathed in an insulated or non-conductive tube.

A plurality of conductive electrodes 202 (FIG. 2) are nestled within cannula 104. In some embodiments cannula 104 comprises 3 electrodes, while in other embodiments, 6, 10, or 12 electrodes are nestled within cannula 104. Any other number of electrodes can also be used and are within the scope of the present disclosure. The electrodes 202 are connected to the electrical terminal 118 at the proximal end of handle 108. Terminal 118 can be connected to a power source (not shown). RF current is conducted from the power source through terminal 118 to electrodes 202.

Figure 2:
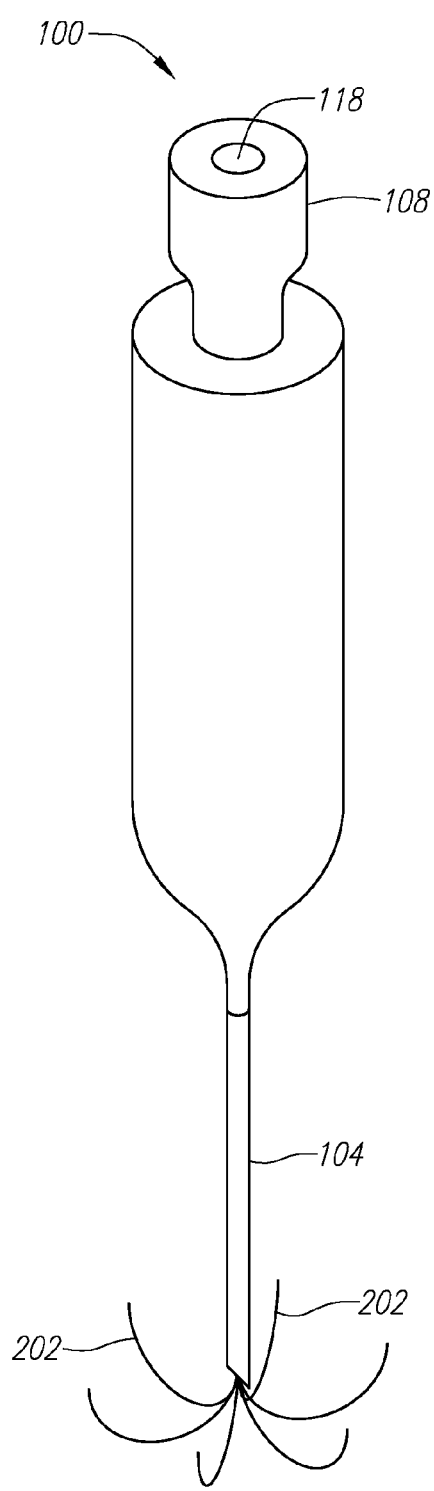
FIG. 2 shows the RF probe of FIG. 1 with its electrodes extended.

As shown in FIG. 2, during the operation of the probe 100, described in greater detail below, the operator pushes handle 108 down, towards the distal end of probe 100, which cause plunger 110 to move down. Plunger 110 pushes electrodes 202 out of the distal end 106 of cannula 104. The maximum downward movement of plunger 110 is reached when the bottom surface 114 of handle 108 abuts against the top surface 116 of handle 102.

Electrodes 202 are preferably formed of spring wire or other material which will retain memory. An array is formed with each electrode 202 arching from cannula 104 in a general "U" shape with each electrode substantially uniformly separated, as shown in FIG. 2. Thus, an array is formed of a plurality of electrodes 202 curving radially outwardly from the axis of distal end 106 of cannula 104. Electrodes 202 all extend a length such that a portion of each electrode 202 is perpendicular to the axis of cannula 104, and preferably continue curving rearwardly back upon themselves such that the distal ends of electrodes 202 are oriented generally parallel to the axis of the cannula 104.

Because electrodes 202 are formed of spring steel, they may be drawn within cannula 104 by drawing handle 108 and plunger 110 up, i.e., away from the distal end of probe 100. Once the distal end 106 of cannula 104 is in position within the patient, sliding electrodes 202 downward through cannula 104 will permit the memory of the wires to take the radially disposed shape of the array shown in FIG. 2.

A safety lock 112 is provided to prevent the accidental extension of electrodes 202. Safety lock 112 is of a substantially semicylindrical shape and can be snapped in between the bottom surface 114 of handle 108 and the top surface 116 of handle 102. When safety lock 112 is in place, plunger 110 cannot move downward. After the distal end 106 of cannula 104 is in place within the patient, the operator can remove safety lock 112 and push plunger 110 downward.

In some embodiments, distal end 106 of cannula 104 is not a sharpened point. In these embodiments, to introduce an electrode array, a conventional sheath and obturator/stylet assembly is introduced percutaneously (through the skin) so that a distal end of the sheath lies at or within a target site, such as a treatment region. In some embodiments, when a surgeon has cut through the skin to reach the organ of interest, the stylet is not introduced percutaneously. Instead the stylet is introduced into the organ of the interest. The stylet is then withdrawn from the sheath, leaving an access lumen to the target site. A delivery probe incorporating electrodes 202 is then introduced through the access lumen of the sheath so that a distal end of an outer cannula of the probe lies near the distal end of the sheath. Electrodes 202 are then extended distally from the distal end of the probe.

Figure 3:
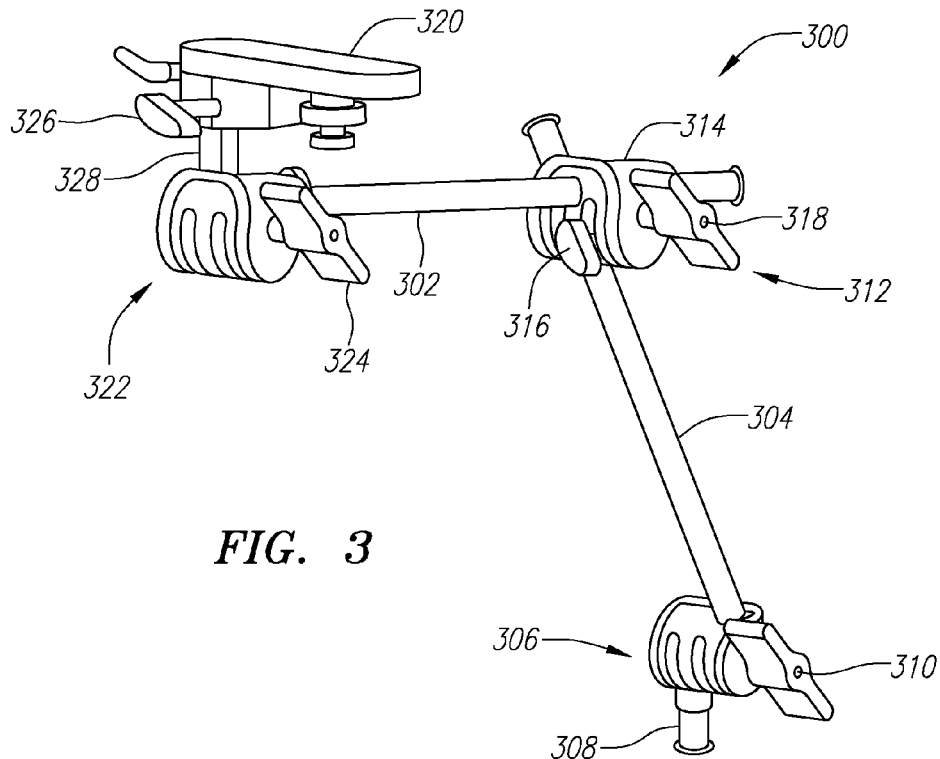
FIG. 3 shows an embodiment of a probe holder.
Figure 4:
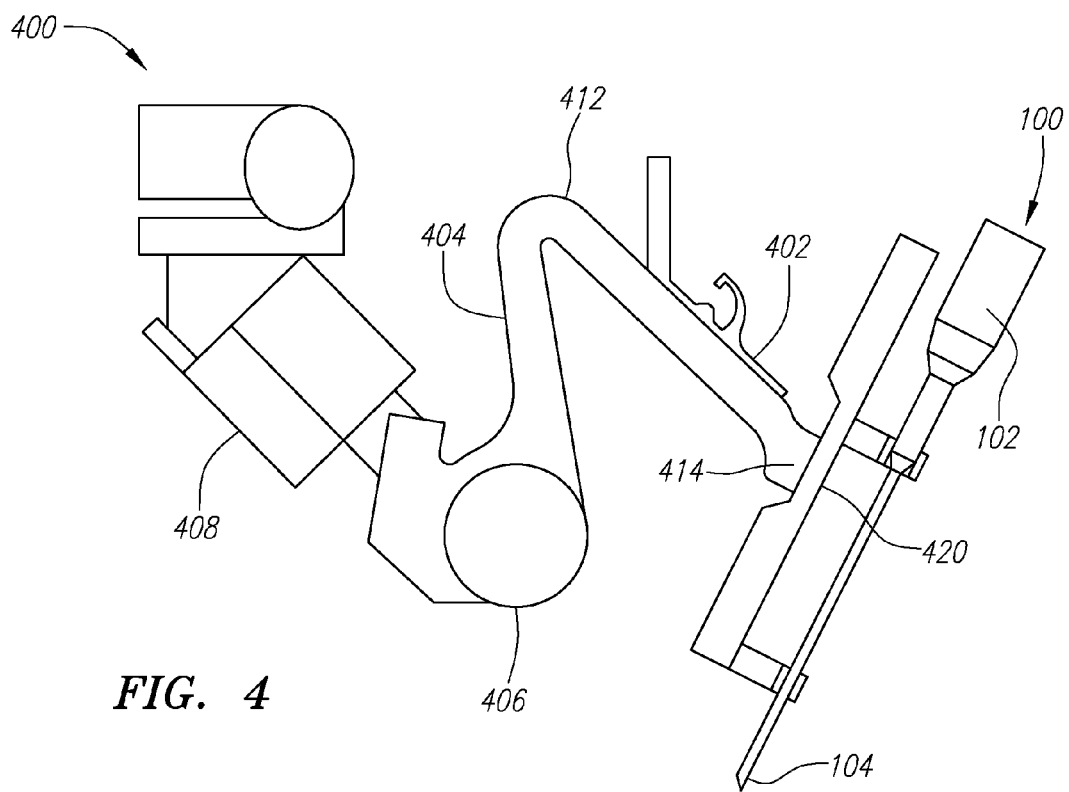
FIG. 4 shows an alternative embodiment of a probe holder.

FIGS. 3 and 4 show examples of a probe holder. As seen in FIG. 3, the probe holder 300 attaches to the patient's bed and secures probe 100 in place. Probe holder 300 comprises two main shafts 302 and 304. Connector 308 is attached to an immobilized object, such as the patient's bed, a railing, or a frame on the patient's bed. Joint 306 allows shaft 304 to move in various directions and be placed in a desired location. Once shaft 304 is in the desired location, joint 306 is locked in place by lock 310.

Joint 312 comprises tube locks 314 and 316, which hold shafts 302 and 304, respectively, in place. Shaft 302 can move in and out of tube lock 314 to increase or decrease the distance between joint 312 and joint 322. Similarly, shaft 304 can move up and down tube lock 316 to increase or decrease the distance between joint 312 and joint 306. Furthermore, joint 312 can rotate about an axis perpendicular to both shafts 302 and 304 to change the angle between shafts 302 and 304. Rotating joint 312 clockwise increases the angle between shafts 302 and 304, while rotating joint 312 counterclockwise decreases the angle between shafts 302 and 304. In addition, shaft 302 can rotate about the axis of shaft 304 at the point of tube lock 316. Shaft 302 can also rotate about its longitudinal axis when tube lock 314 is unlocked. Once a desired combination of distance between joints 306 and 312 and joints 322 and 312 and angle between shafts 302 and 304 is obtained, joint 312 is locked in place by lock 318.

Probe 100 (not shown) is attached to probe holder 300 at connector 320. In some embodiments, handle 102 of probe 100 is connected to probe holder 300, while alternatively, cannula 104 can be connected to probe holder 300. Any part of probe 100 can be attached to probe holder 300 to immobilize probe 100. Connector 320 is attached to joint 322 through axis 328 and can rotate about axis 328 in a full circle and be lock in place by lock 326. Joint 322 can rotate about an axis perpendicular to both shaft 302 and axis 328. Lock 324 locks joint 322 at the desired location.

Thus, once probe 100 is attached to probe holder 300 at connector 320, and probe holder 300 is attached to the patient's bed through connector 308, the degrees of freedom offered by joints 306, 312, and 322, tube locks 314 and 316, and axis 328 allows the operator to place probe 100 at any desired angle and at any desired distance from the patient's body.

FIG. 4 depicts another embodiment of a probe holder 400, where probe 100 is shown attached to probe holder 300 by connector 420. Probe holder 400 is connected to the patient's bed through connector 408. Similar to the probe holder 300 discussed above with respect to FIG. 3, probe 100 can be placed at any desired location by taking advantage of the degrees of freedom offered by joints 406, 412, and 414, which allow the operator to change the angle between shafts 402 and 404.

Figure 5:
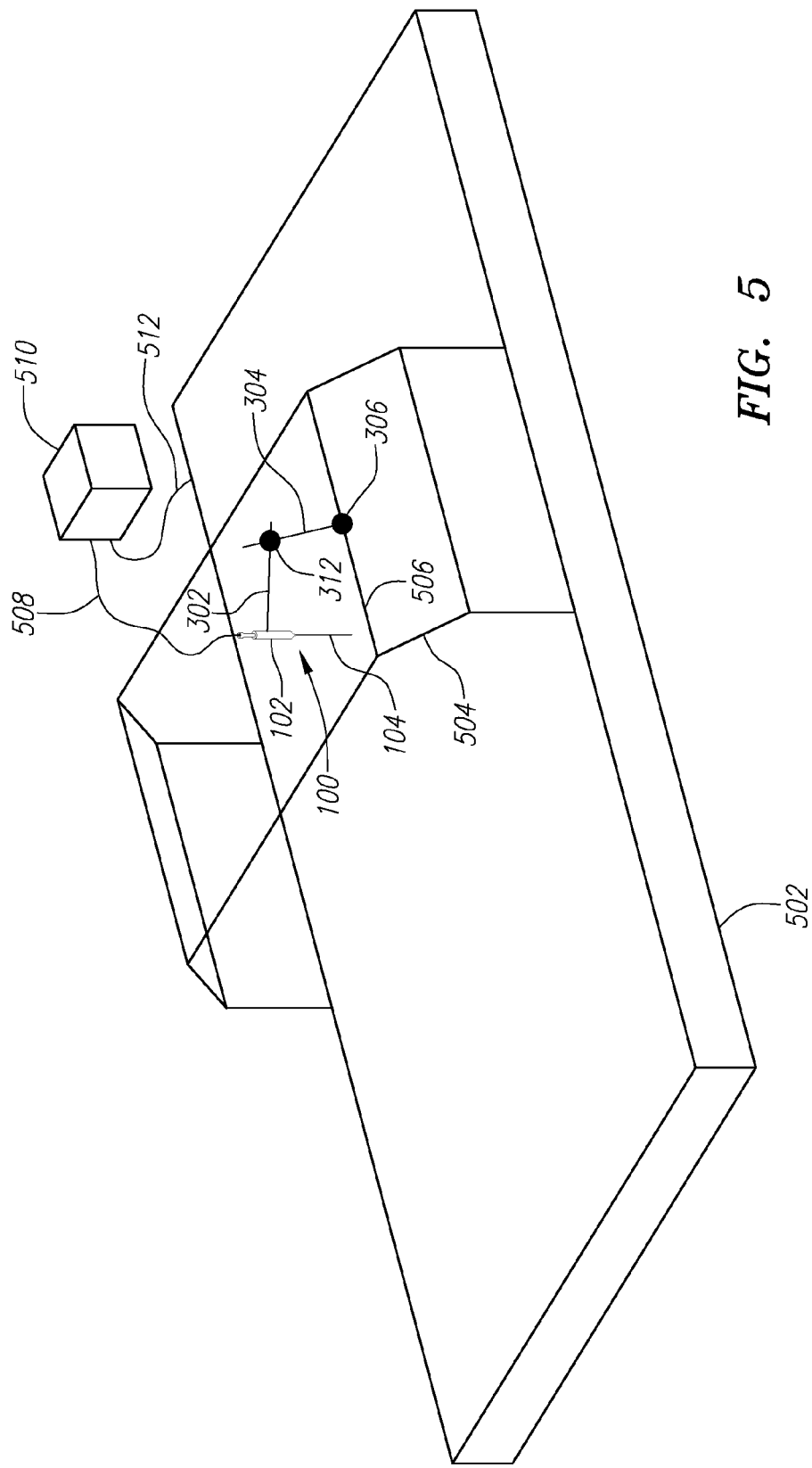
FIG. 5 shows an embodiment of surgical bed with an RF probe connected to a frame lattice located over the bed.

Referring now to FIG. 5, a patient's bed 502 is depicted. Bed 502 is primarily used during surgery or to hold the patient during radiation therapy. A frame lattice 504 is placed over bed 502. Frame lattice 504 is commonly used to immobilize the patient during radiation therapy. An example of bed 502 having frame lattice 504 is the bed used in connection with BodyFIX® patient positioning system, marketed by Medical Intelligence (http://medical-intelligence.com).

As shown in FIG. 5, probe holder 300, or similarly probe holder 400 or any similar device, is attached to frame lattice 504, for example at a cross-bar 506. Probe 100 is then connected to probe holder 300. Probe holder 300 can be connected to any immobile object, such as bed 502, any part of frame lattice 504, or an immobile object not connected with bed 502. The immobile object is preferably in close proximity to the patient so that probe 100 can be placed over the area of interest on the patient's body. By "immobile" with respect to the immobile object, it is meant that the object does not move when the patient makes voluntary or involuntary movements, such as breathing, heart beat, muscle twitches, gastrointestinal movements, or small shifts in position.

Wire 508 provides electrical connection between probe 100 and power source 510. In some embodiments, the RF current flows between the several electrodes 202. In these embodiments, at least one electrode 202 serves to return the current to power source 510. Wire 508 also comprises two wires, one for taking the current to electrodes 202 and one for returning the current. Alternatively, a return wire 512 is connected to bed 502 or to the patient. In these embodiments, the current flows from power source 510 through wire 508 to electrodes 202, through the patient and then returns to power source 510 through wire 512.

Figure 6A:
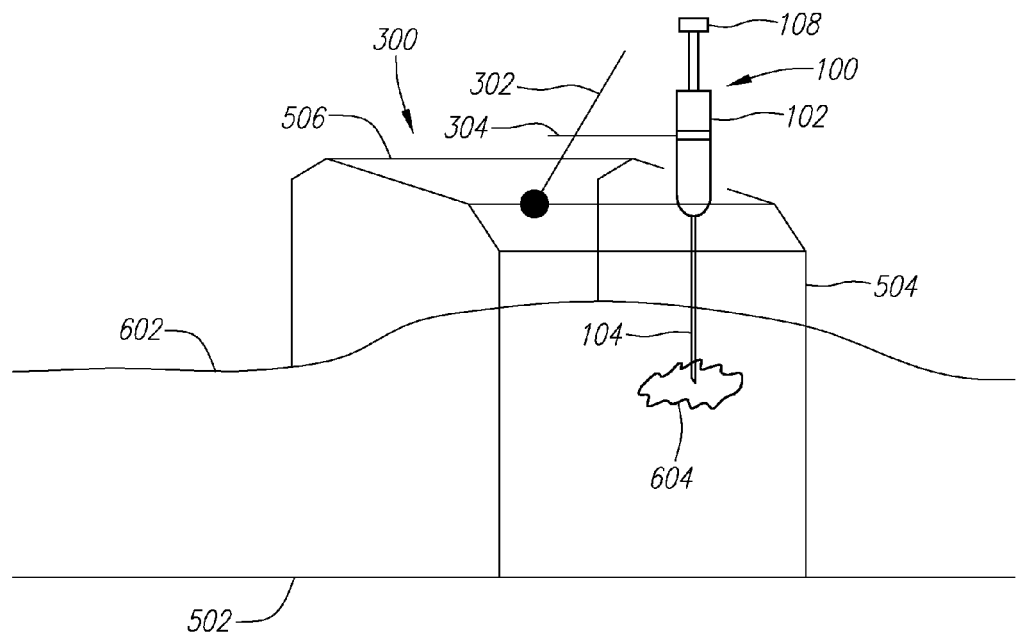
FIG. 6A depicts the step of inserting the cannula of an RF probe into a treatment region inside a patient's body.

Referring now to FIG. 6A, a patient 602 is shown lying on a bed 502 under a frame lattice 504. A probe holder 300 is connected to a cross-bar 506 of frame lattice 504. Shaft 302 of probe holder 300 is connected directly to cross-bar 506, while shaft 304 is connected to handle 102 of probe 100. The figure shows cannula 104 has been inserted into the patient's body and distal end 106 of cannula 104 is located within a treatment region 604. The treatment region 604 can be a tumor, such as a malignant tumor or a benign tumor. Typically, the treatment region 604 is a tissue type that needs to be removed, or its sized decreased, by heating and radiation therapy.

It is understood by those of ordinary skill in the art that probe 100 can be secured to frame lattice 504 at anytime during this procedure. Thus, in some embodiments, the health care provider secures probe 100 to frame lattice 504 prior to the extension of electrodes 202 and the application RF current. In alternative embodiments, probe 100 is secured to frame lattice 504 subsequent to the extension of electrodes 202. In other alternative embodiments, probe 100 is secured to frame lattice 504 after the termination of the application of RF current and the heating of the tumor, but prior to the irradiation of the tumor.

Figure 6B:
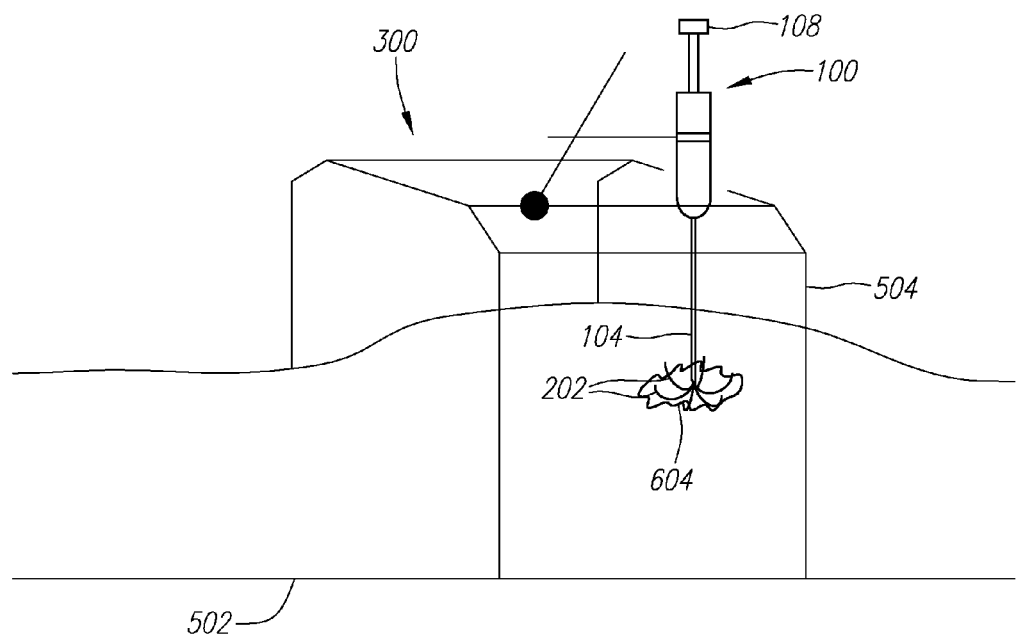
FIG. 6B depicts the step of extending the electrodes of an RF probe into a treatment region inside a patient's body.

As shown in FIG. 6B, handle 108 of probe 100 is pushed downward, i.e., towards the distal end of probe 100. Electrodes 202 extend outwardly from distal end 106 of cannula 104 and into treatment region 604. Electrodes 202 heat treatment region 604 when RF current is applied. Typically, treatment region 604 is heated to temperatures high enough that cause cell death, such as a temperature of greater than 50° C. The heating causes cells, such as malignant or cancerous cells, within treatment region 604, to die, thereby reducing the size of treatment region 604.

Figure 6C:
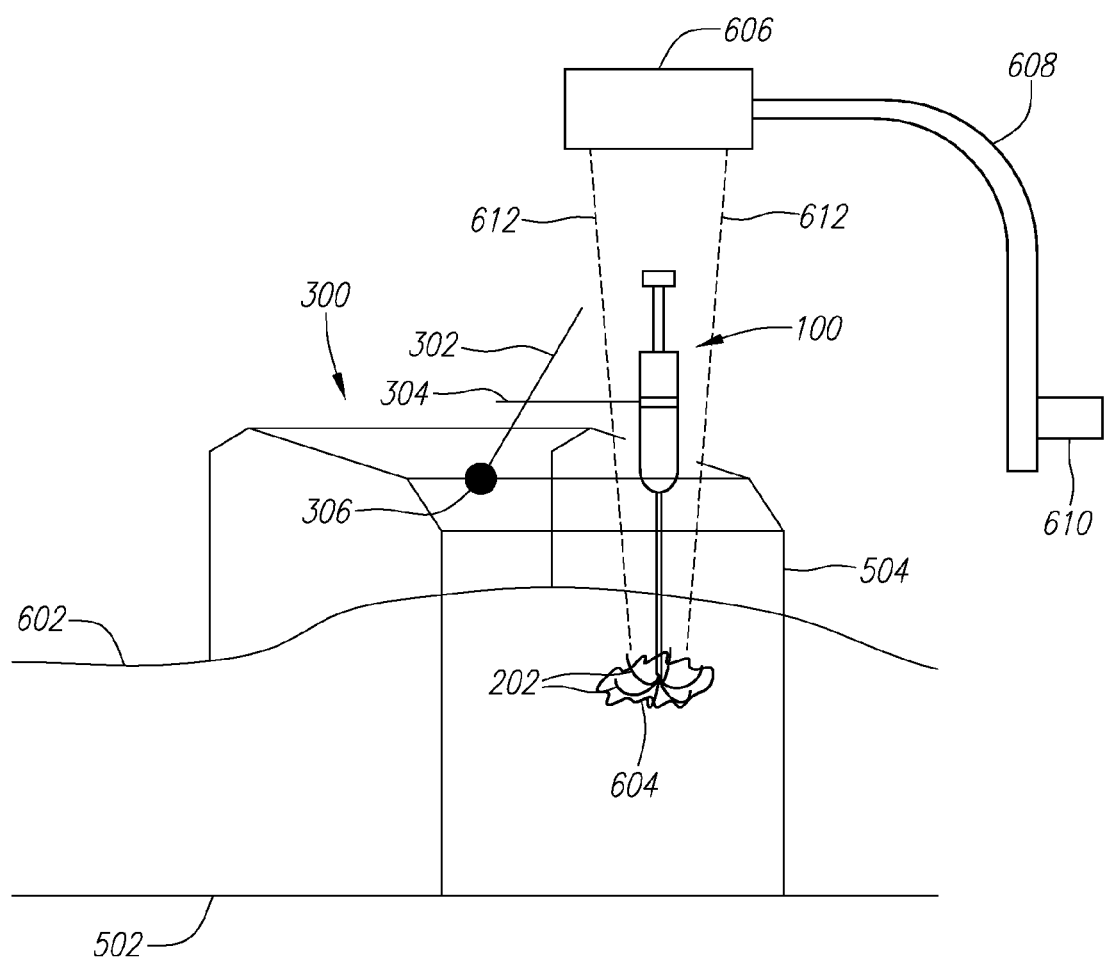
FIG. 6C depicts the step of holding the treatment region immobile as the treatment region is irradiated.

After the heating is complete, the RF current is turned off. The patient 602 remains on bed 502 and cannula 104 with the extended electrodes 202 remain in patient's body. As shown in FIG. 6C, the patient is then placed under a radiation source 606 and radiation 612 is then applied to treatment region 604. The radiation is typically an ionizing radiation commonly used for the treatment of cancerous tissue. Examples of radiation used for cancer treatment include, but are not limited to, x-rays, gamma rays, electron beams, protons, neutrons, alpha particles, and beta particles. The radiation source 606 is typically connected to a pivot 610 by a curved arm 608. During the course of irradiation, radiation source 606 rotates in a substantially semicircular path around the patient and about the pivot 610.

Electrodes 202 are rigidly connected to probe 100, which in turn is rigidly connected to probe holder 300 and frame lattice 504. Electrodes 202, therefore, are substantially immobilized even if the body of the patient moves due to breathing, heart beats, involuntary twitches, or gastrointestinal movements.

Because a plurality of electrodes 202 are extended into treatment region 604 a greater force is necessary to dislodge electrodes 202 from treatment region 604 than if a single needle was used. For example, 0.110 kg of force is required to pull a single-needle probe out of lung tissue. Tine-based probes, such as the ones described herein, require a force of between 0.375-0.580 kg to be pulled out of lung tissue. The higher force ensures that the probe stays within the patient and is not displaced accidentally. In addition, the higher force required to remove the probe ensures that electrodes 202 hold treatment region 604 in place rigidly and substantially minimize the movement of treatment region 604 as the patient's body moves. The extended probes 202, therefore, ensure that the movement of treatment region 604 is minimized during the radiation therapy step.

In some embodiments, electrodes 202 are at least partially extended into the treatment region 604 to secure the tissue in place. Electrodes 202 need not be fully extended. Partial extension of electrodes 202 still provides the necessary hold on the treatment region 604 to minimize the movement of treatment region 604 during the irradiation step.

What is claimed is:

1. A method of treating a treatment region within solid tissue of a patient using, a probe, the probe having a cannula and a handle, the cannula having a distal end, the method comprising
    introducing the cannula through tissue of the patient until the distal end of the cannula is located proximate to the treatment region, wherein a plurality of electrodes is disposed within the cannula while the cannula is introduced through the tissue;
    advancing the plurality of electrodes out of the distal end of the cannula into the treatment region;
    delivering energy through the plurality of electrodes;
    attaching the cannula to a probe holder and attaching the probe holder to an immobile object, wherein the probe holder and immobile object are both external to the patient to thereby substantially minimize movement of the treatment region with respect to the immobile object when the patient makes voluntary or involuntary movements that would otherwise cause movement of the treatment region with respect to the immobile object; and
    irradiating the treatment region with a therapeutically effective dose of an ionizing radiation from an externally located source while the plurality of electrodes remain at least partially advanced within the treatment region and while the cannula remains attached to the probe holder.

2. The method of claim 1, wherein the treatment region is a malignant tumor.

3. The method of claim 1, wherein the plurality of electrodes are advanced in a generally distal direction from the distal end of the cannula within the treatment region.

4. The method of claim 3, wherein distal ends of the electrodes diverge, curve radially outwardly, and evert to form a three-dimensional pattern from the distal end of the cannula.

5. The method of claim 3, wherein the plurality of electrodes are advanced symmetrically about an axis extending from the distal end of the cannula into the treatment region.

6. The method of claim 1, wherein energy is delivered by establishing radio frequency current flow among the plurality of electrodes or between the plurality of electrodes and a return electrode.

7. The method of claim 1, wherein, after the cannula is attached to the probe holder and the plurality of electrodes are advanced into the treatment region, the plurality of electrodes hold the treatment region substantially stationary relative to the distal end of the cannula.

8. The method of claim 1, wherein the handle is secured to the immobile object to hold the distal end of the cannula substantially stationary relative to the immobile object.

9. The method of claim 1, wherein the cannula is attached prior to delivering energy.

10. The method of claim 1, wherein the ionizing radiation is selected from the group consisting of x-ray, gamma ray, electron beam, protons, neutrons, alpha particles, and beta particles.

11. The method of claim 1, wherein the externally located source of ionizing radiation rotates in a substantially semicircular path around the patient.

12. A method of treating a treatment region within a patient using a probe, the probe having a cannula and a handle, the cannula having a distal end, the method comprising
    introducing the cannula through tissue of the patient until the distal end of the cannula is located proximate to the treatment region, wherein a plurality of electrodes is disposed within the cannula while the cannula is introduced through the tissue;
    advancing the plurality of electrodes out of the distal end of the cannula into the treatment region;
    delivering energy through the plurality of electrodes;
    attaching the cannula to a probe holder and attaching the probe holder to an immobile object, wherein the probe holder and immobile object are both external to the patient to thereby substantially minimize movement of the treatment region with respect to the immobile object when the, patient makes voluntary or involuntary movements that would otherwise cause movement of the treatment region with respect to the immobile object; and
    irradiating the treatment region with a therapeutically effective dose of an ionizing radiation from an externally located source while the plurality of electrodes remain at least partially advanced within the treatment region and while the cannula remains attached to the probe holder.

13. The method of claim 12, wherein the treatment region is a malignant tumor.

14. The method of claim 12, wherein the treatment region comprises one of lung tissue, liver tissue, breast tissue, and tissue within the abdominal cavity.

15. The method of claim 11, wherein the plurality of electrodes are advanced in a generally distal direction from the distal end of the cannula within the treatment region, wherein distal ends of the electrodes diverge, curve radially outwardly, and evert to form a three-dimensional pattern from the distal end of the cannula.

16. The method of claim 12, wherein the immobile object is a bed frame.

17. The method of claim 12, further comprising retracting the plurality of electrodes into the cannula and removing the cannula from the patient after irradiating the treatment region.

18. The method claim 12, wherein the externally located source of ionizing radiation rotates in a substantially semicircular path around the patient.

19. A method of treating a treatment region within solid tissue of a patient using a probe, the probe having a cannula and a handle, the cannula having a distal end, the method comprising
    introducing the cannula into the solid tissue of the patient until the distal end of the cannula is located proximate to the treatment region, wherein a plurality of electrodes is disposed within the cannula while the cannula is introduced through the solid tissue;
    advancing the plurality of electrodes out of the cannula into the solid tissue in a generally distal direction from the distal end of the cannula within the treatment region, wherein the electrodes diverge, curve radially outwardly, and evert to form as three-dimensional pattern from the distal end of the cannula, whereby the plurality of electrodes hold the treatment region substantially stationary relative to the distal end of the cannula; establishing radio frequency current flow among the plurality of electrodes;

attaching the cannula to a probe holder and attaching the probe holder to an immobile object, wherein the probe holder and immobile object are both external to the patient to thereby substantially minimize movement of the treatment region with respect to the immobile object when the patient makes voluntary or involuntary movements that would otherwise cause movement of the treatment region with respect to the immobile to the object;

irradiating the treatment region with a therapeutically effective dose of an ionizing radiation from an externally located source while the plurality of electrodes remain at least partially advanced within the treatment region and while the cannula remains attached to the probe holder; and retracting the plurality of electrodes into the cannula and removing the cannula from the patient after irradiating the treatment region.

20. The method of claim 19, wherein the treatment region is a malignant tumor.

21. The method of claim 19, wherein the solid tissue is selected from the group consisting of lung, liver, breast, and tissue within the abdominal cavity.

22. The method of claim 19, wherein the immobile object is a bed frame.

23. The method of claim 19, wherein the externally located source of ionizing radiation rotates in a substantially semicircular path around the patient.

* * * * *